(12) United States Patent
Chang et al.

(10) Patent No.: US 10,768,155 B2
(45) Date of Patent: Sep. 8, 2020

(54) MULTIMODAL ANALYTE SENSOR NETWORK

(71) Applicant: INTERNATIONAL BUSINESS MACHINES CORPORATION, Armonk, NY (US)

(72) Inventors: Josephine B. Chang, Bedford Hills, NY (US); Hendrik F. Hamann, Yorktown Heights, NY (US); Levente Klein, Tuckahoe, NY (US); Siyuan Lu, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/242,364

(22) Filed: Jan. 8, 2019

(65) Prior Publication Data
US 2019/0137468 A1 May 9, 2019

Related U.S. Application Data

(62) Division of application No. 15/049,280, filed on Feb. 22, 2016, now Pat. No. 10,209,234.

(51) Int. Cl.
*G01N 33/00* (2006.01)
(52) U.S. Cl.
CPC .................. *G01N 33/0075* (2013.01)
(58) Field of Classification Search
CPC ............... G01N 27/27; G01N 33/0075; G01N 33/0031; G01N 33/0032; G01N 33/0034; G01N 33/0036; G01N 33/4836
See application file for complete search history.

(56) References Cited

U.S. PATENT DOCUMENTS

| 6,435,860 | B1 | 8/2002 | Brookshire et al. |
| 8,307,785 | B2 | 11/2012 | Zimmerman et al. |
| 9,030,329 | B2 | 5/2015 | Rutherford et al. |
| 2006/0282225 | A1 | 12/2006 | Sunshine et al. |
| 2012/0206715 | A1 | 8/2012 | Laub |

(Continued)

OTHER PUBLICATIONS

Niu et al. "The Design and Evaluation of a Wireless Sensor Network for Mine Safety Monitoring." Global Telecommunications Conference, 2007. Globecom'07, IEEE, 2007, 5 Pages.

(Continued)

*Primary Examiner* — Gurpreet Kaur
(74) *Attorney, Agent, or Firm* — Richard A. Wilhelm

(57) ABSTRACT

The present invention involves a multimodal sensor network for analyte detection. A first mode may involve low-power detection and a second mode may involve determining an analyte concentration and transmitting data associated with the analyte concentration. Specifically, the first mode may include establishing an analyte sensor network in a detection region, detecting an analyte in the detection region, and generating an electrical signal in response to the detecting the analyte. In response to the electrical signal exceeding a first threshold, the analyte detection system may operate in the second mode. The second mode may include requesting data associated with the one or more environmental conditions, determining an analyte concentration based on one or more environmental conditions transmitting data associated with the analyte concentration.

9 Claims, 10 Drawing Sheets

(56) References Cited

U.S. PATENT DOCUMENTS

2015/0226585 A1 8/2015 Yang
2016/0299111 A1* 10/2016 de Kontz ........... G01N 33/0075
2017/0241936 A1 8/2017 Chang et al.
2017/0248514 A1* 8/2017 Pavey ................ G01N 33/0057

OTHER PUBLICATIONS

Boulart et al., "Sensors and Technologies for In Situ Dissolved Methane Measurements and Their Evaluation Using Technology Readiness Levels." TrAC Trends in Analytical Chemistry 29.2 (2010): 10 pages.
Zhang et al., "Design a Wireless Sensor Network for Methane Monitoring System." Industrial Informatics, 2008. INDIN 2008. 6th IEEE International Conference on. IEEE, 2008, 5 pages.
Tumer et al., "Design of a Methane Monitoring System Based on Wireless Sensor Networks." Sci. Res. Essays 5 (2010): 7 Pages.
IBM: List of IBM Patents or Patent Applications Treated As Related (Appendix P), Jan. 9, 2019, pp. 1-2.
Pending U.S. Appl. No. 16/242,488, filed Jan. 8, 2019, entitled "Multimodal Analyte Sensor Network", pp. 1-56.

* cited by examiner

500

```
┌─────────────────────────────────────────────┐
│ Establish an analyte sensor network in a    │
│ detection region.                           │
│ 504                                         │
└─────────────────────────────────────────────┘
                      │
                      ▼
       ┌ ─ ─ ─ ─ ─ ─ ─ ─ ─ ─ ─ ─ ─ ─ ─ ─ ─ ─ ─ ┐  502
       ┌─────────────────────────────────────┐
       │ Detect an analyte in the detection  │
       │ region.                             │
       │ 508                                 │
       └─────────────────────────────────────┘
                      │
                      ▼
       ┌─────────────────────────────────────┐
       │ Generating an electrical signal in  │
       │ response to the detecting the       │
       │ analyte.                            │
       │ 512                                 │
       └─────────────────────────────────────┘
                      │
                      ▼
         < Does the electrical signal          >── No
           exceed a first threshold?
           516
                      │ Yes
                      ▼
       ┌ ─ ─ ─ ─ ─ ─ ─ ─ ─ ─ ─ ─ ─ ─ ─ ─ ─ ─ ─ ┐
       ┌─────────────────────────────────────┐
       │ Receive data associated with the    │
       │ one or more environmental           │
       │ conditions of the detection region. │
       │ 520                                 │
       └─────────────────────────────────────┘
                      │
                      ▼
       ┌─────────────────────────────────────┐
       │ Determine an analyte concentration  │
       │ based on one or more environmental  │
       │ conditions.                         │
       │ 524                                 │
       └─────────────────────────────────────┘
                      │
                      ▼
         < Does the analyte concentration      >── No
           exceed a second threshold?
           528
                      │ Yes                       518
                      ▼
       ┌─────────────────────────────────────┐
       │ Transmit, by the local gateway,     │
       │ data associated with the analyte    │
       │ concentration.                      │
       │ 532                                 │
       └─────────────────────────────────────┘
```

FIG. 5

MULTIMODAL ANALYTE SENSOR NETWORK

BACKGROUND

The present invention relates generally to the field of analyte detection, and more particularly to a method and sensor network for analyte detection.

Conventional analyte monitoring systems may be unsuitable, and/or prohibitively expensive to implement, for continuous monitoring over a region of a potential analyte source (e.g., a pipeline, drilling site, etc.). Low cost analyte (e.g., methane) sensors may have high minimum detection limits and suffer from signal drift, cross sensitivities with other gases, and poisoning (which may make the sensors inaccurate without regular calibration). Optical-based analyte detectors may have lower minimum detection limits than low cost analyte sensors but may be expensive and consume too much power for wireless sensor network applications.

SUMMARY

Embodiments of the present invention disclose a method for detecting an analyte within a detection region. The method may include detecting an analyte with an analyte sensor network established within the detection region. The analyst sensor network may include a sensor node array and a local gateway. The sensor node array may include at least one first node and a plurality of second nodes distributed throughout the detection region. The at least one first node may include a first analyte sensor and each node of the plurality of second nodes may include a second analyte sensor. The first analyte sensor may have a lower detection limit than the second analyte sensor. Detecting the analyte may include identifying an electrical signal generated in response to the analyte in the detection region. The electrical signal may be generated by an electrochemical reaction of the first analyte sensor or the second analyte sensor. The method may include requesting, based on the electrical signal exceeding a first threshold value, data associated with one or more environmental conditions of the detection region. The method may include determining an analyte concentration based on the one or more environmental conditions. The method may include transmitting, based on the analyte concentration exceeding a second threshold value, data associated with the analyte concentration.

Embodiments of the present invention disclose a system for detecting an analyte in a detection region. The system may include an analyte sensor network in the detection region comprising a sensor node array and a local gateway. The sensor node array may include at least one first node and a plurality of second nodes distributed throughout the detection region. The at least one first node may include a first analyte sensor. Each node of the plurality of second nodes may include a second analyte sensor. The first analyte sensor may have a lower detection limit than the second analyte sensor. The system may include one or more computer processors, one or more computer-readable storage media, and program instructions stored on the computer-readable storage media for execution by at least one of the one or more processors. The program instructions may include instructions to detect the analyte with the analyte sensor network established within the detection region. The instructions to detect the analyte may include instructions to identify an electrical signal generated by an electrochemical reaction of the analyte with one or more portions of the first analyte sensor or the second analyte sensor. The program instructions may include instructions to request, based on the electrical signal exceeding a first threshold value, data associated with one or more environmental conditions of the detection region. The program instructions may include instructions to determine an analyte concentration based on the one or more environmental conditions. The program instructions may include instructions to transmit, based on the analyte concentration exceeding a second threshold value, data associated with the analyte concentration.

Embodiments of the present invention disclose a system for detecting an analyte in a detection region. The system may include an analyte sensor array comprising at least one first node and a plurality of second nodes distributed throughout the detection region. The at least one first node may include an optical sensor. Each node of the plurality of second nodes may include a chemiresistive sensor. The system may include an environmental conditions measuring device, such as, for example, a thermometer, a barometer, a hygrometer, an anemometer, or any combination thereof. The system may include a local gateway configured to communicate with a remote gateway. The system may include a computing device including one or more processors, computer-readable storage media, and program instructions stored on the computer-readable storage media for execution by the processor. The program instructions may include instructions to detect the analyte with the analyte sensor array established within the detection region. The instructions to detect the analyte may include instructions to identify an electrical signal generated by an electrochemical reaction of the analyte with one or more portions of the first analyte sensor and/or the second analyte sensor. The program instructions may include instructions to request, based on the electrical signal exceeding a first threshold value, data associated with one or more environmental conditions of the detection region. The program instructions may include instructions to determine an analyte concentration based on the one or more environmental conditions. The program instructions may include instructions to transmit, based on the analyte concentration exceeding a second threshold value, data associated with the analyte concentration.

BRIEF DESCRIPTION OF THE SEVERAL VIEWS OF THE DRAWINGS

The following detailed description, given by way of example and not intended to limit the invention solely thereto, will best be appreciated in conjunction with the accompanying drawings.

FIG. 5 is a flowchart depicting operational steps of an analyte monitoring program, in accordance with an embodiment of the present invention.

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

Embodiments of the present invention may involve a system and method of a sensor network for analyte detection. Conventional analyte sensor networks may rely on centralized communications where each node sends information to a central gateway to aggregate and analyze data. This process may involve frequent data streaming from sensing nodes to a gateway. Analytics, such as analysis of an analyte concentration, may be carried out at the gateway or in a data center and then transmitted to a radio at the sensing nodes. This may require frequent radio communication at the sensing nodes, increasing power consumption and, in the case of battery-operated sensing nodes, reducing battery life of the sensing nodes.

Embodiments of the present invention may involve a system (e.g., a sensor network) and method for analyte detection having a combination of at least one high performance sensor mote (e.g., including an optical sensor) and a plurality of low cost sensor motes (e.g., including a chemiresistive sensor). A sensor mote may be a node in a sensor network including one or more devices, such as, for example, a sensor, communication device, gateway, environmental conditions sensor, computing device, or any combination thereof. In an embodiment, the sensor network may include a weather station which may, for example, indicate direction and speed of the wind flow. In an embodiment, a series of low cost sensor motes may be spatially distributed over a region of a potential analyte source (e.g., a pipeline, production site, etc.) where each low cost sensor mote is a distance (e.g., ranging from 1 meter to 15 kilometers and ranges therebetween) from one or more neighboring low cost sensor motes. In an embodiment, a high performance sensor mote may be located within a detection region. The sensor may acquire the signal continuously or following a well-defined protocol that may be related to, for example, a wind direction or a measurement from another sensor node. A combination of at least one high performance sensor mote and a plurality of low cost sensor motes spatially distributed over a region of a potential analyte source (i.e. a detection region) may be cheaper and consume less power than conventional analyte detection systems covering the region of the potential analyte. Embodiments of the present invention will now be described in detail with reference to FIGS. 1-6.

Figure 1:
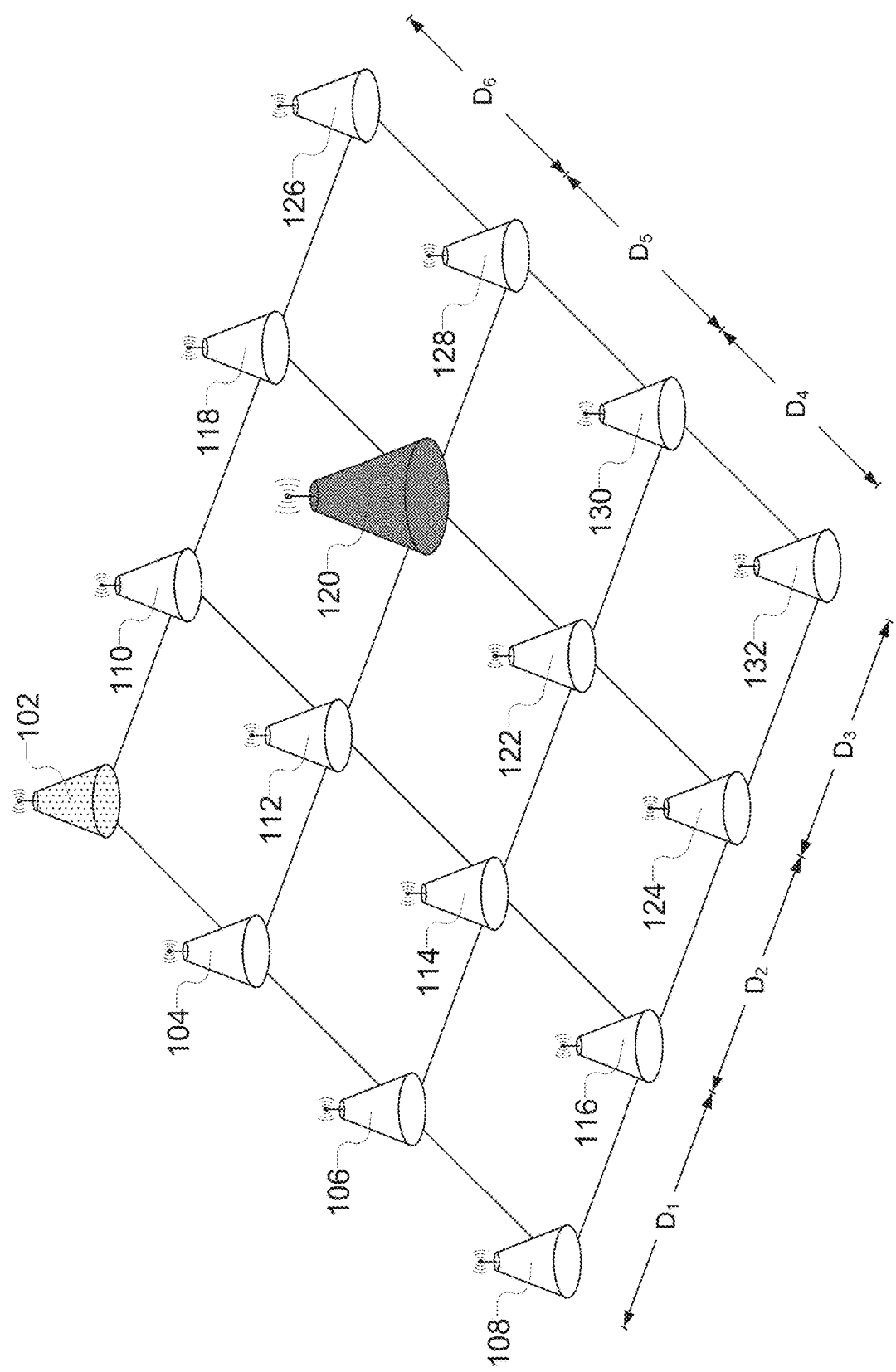
FIG. 1 is a functional block diagram illustrating an analyte monitoring system, in accordance with an embodiment of the present invention.

FIG. 1 is an analyte monitoring system 100, according to an aspect of the invention. In an exemplary embodiment, the analyte monitoring system 100 may include an analyte sensor network in a detection region including a sensor node array and a local gateway node 120. In another embodiment, the analyte monitoring system 100 may include the sensor node array, the local gateway node 120, and an environmental conditions sensor. The sensor node array may include at least one first node (e.g., first node 102) and a plurality of second nodes (e.g., second node 104, second node 106, second node 108, second node 110, second node 112, second node 113, second node 116, second node 118, second node 122, second node 124, second node 126, second node 128, second node 130, and second node 132) distributed throughout the detection region. The at least one first node may include a first analyte sensor. Each node of the plurality of second nodes may include a second analyte sensor. The first analyte sensor may have a lower detection limit than the second analyte sensor.

In an embodiment, the analyte monitoring system 100 may include an environmental conditions sensor (e.g., a weather station) which may be an independent node or included in another node. For example, the environmental conditions sensor may be included within the local gateway node 120, the first node 102, the second node 104, or any combination of nodes. The environmental conditions sensor may measure, for example, wind direction, wind direction, temperature, humidity, or any combination of environmental conditions. In an embodiment, an analyte sensor may be mounted on top of the environmental conditions sensor which may enable the analyte sensor to detect an analyte more easily than if mounted in a lower position, such as, for example, at ground level.

Nodes of the sensor node array may be distributed throughout a detection region. The detection region may be a location where a potential leak of an analyte may occur, such as, for example, a region in and/or around a mine (e.g., region around a hydraulic fracturing operation, coal mine, etc.), a region around a pipeline (e.g., region around a natural gas pipeline), or a region around a geological emission source (e.g., volcano, sea floor vent, geyser, etc.). The nodes may be distributed throughout the detection region a distance apart from one another. For example, the second node 108 may be a distance $D_1$ from the second node 116, the second node 116 may be a distance $D_2$ from the second node 124. The distances may be the same distance or a different distance. The distances may range from approximately 1 meter to approximately 15 kilometers, and ranges therebetween. The ranges therebetween may include, for example, 5 to 10 meters, 15 to 25 meters, 50 to 60 meters, etc. Each distance may depend on one or more variables, such as, for example, a characteristic of an analyte, one or more known and/or expected environmental conditions, a characteristic of the detection region (e.g., topography or vegetation cover), a detection limit of one or more analyte sensors, a population of the detection region (e.g., a detection region in and/or near a city may involve smaller distances between nodes), energy consumption per node, energy generation per node (e.g., via solar cells), or any combination thereof.

In an embodiment, the analyte monitoring system 100 may include a network. The network may be any combination of connections and protocols that will support communications between the nodes (e.g., between the first node 102 and the local gateway node 120). In an embodiment, the network may have a network topology in which each node can relay data for the network (i.e. a mesh network). In another embodiment, each node may be connected to a common central node (i.e. a star network). For example, each node (e.g., first node 102 and second node 104) may be connected to the local gateway node 120. The network may include, for example, wired connections, wireless connections, or a combination thereof. In other embodiments, the network may be implemented as a personal area network (PAN), a local area network (LAN), a metropolitan area network (MAN), a wide area network (WAN), a global area network (GAN), or any combination of networks.

In an embodiment, each node of the analyte monitoring system 100 may include a communication device to enable data transmission in the network. The communication device may include, for example, a near-field communication (NFC) device, an Institute of Electrical and Electronics Engineers (IEEE) 802.11 device (e.g., Wi-Fi), an IEEE 802.16 device (e.g., WiMAX), a Long Term Evolution (LTE) device, a microwave transmission device, or any combination thereof. The communication device may be included in one or more nodes (e.g., the first node 102, the second node 104, the locate gateway node 120, etc.).

In an embodiment, the analyte monitoring system 100 may include an analyte monitoring application. The analyte monitoring application may be a program, function, or module of a computer program (not shown) executable by a processor of the analyte monitoring system 100. In an embodiment, the analyte monitoring program may be executable by a processor within one or more nodes (e.g., first node 102, second node 104, and/or local gateway node 120) of the analyte monitoring system 100.

Figure 2A:
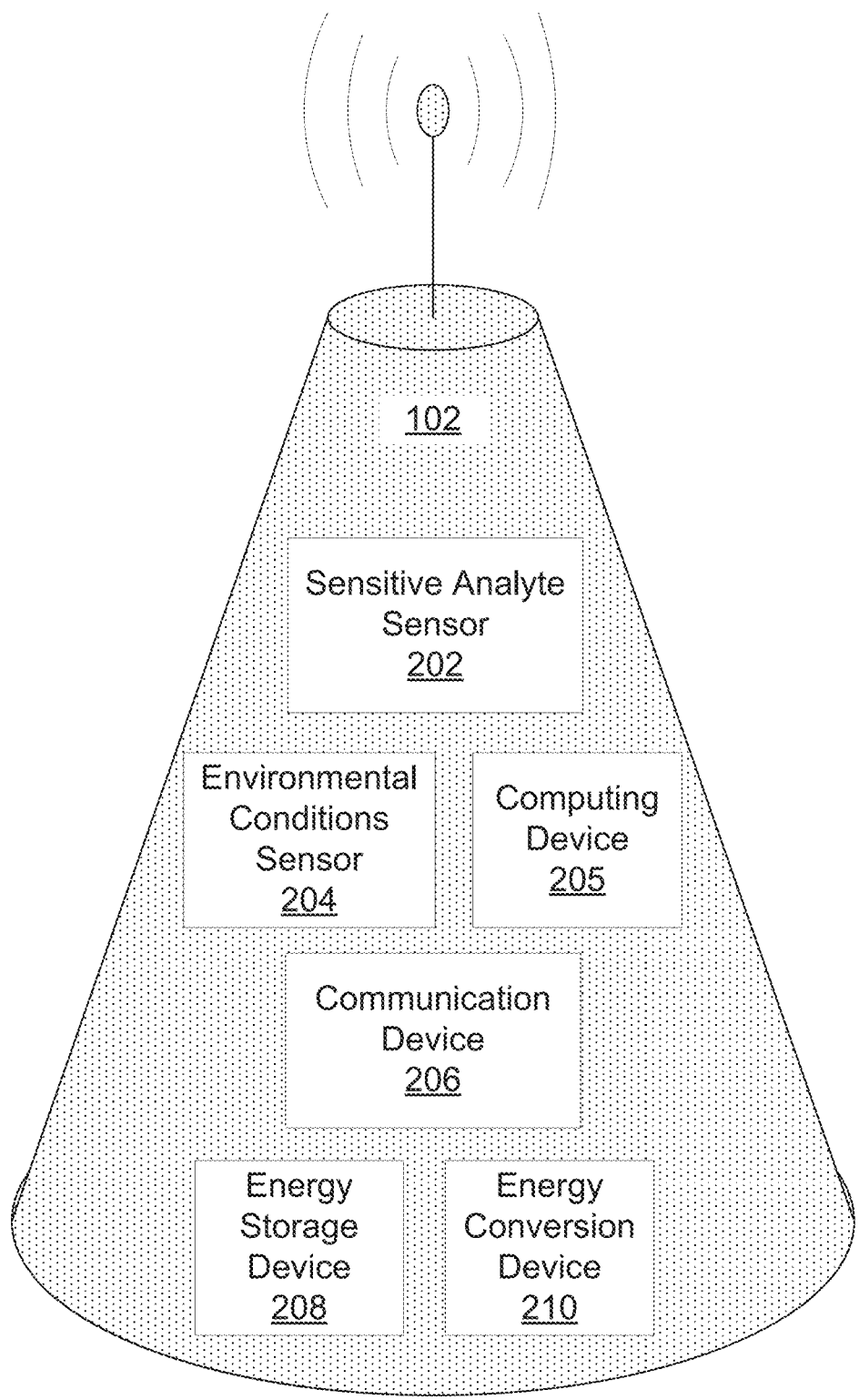
FIG. 2A illustrates a first node, in accordance with an embodiment of the present invention.
Figure 2B:
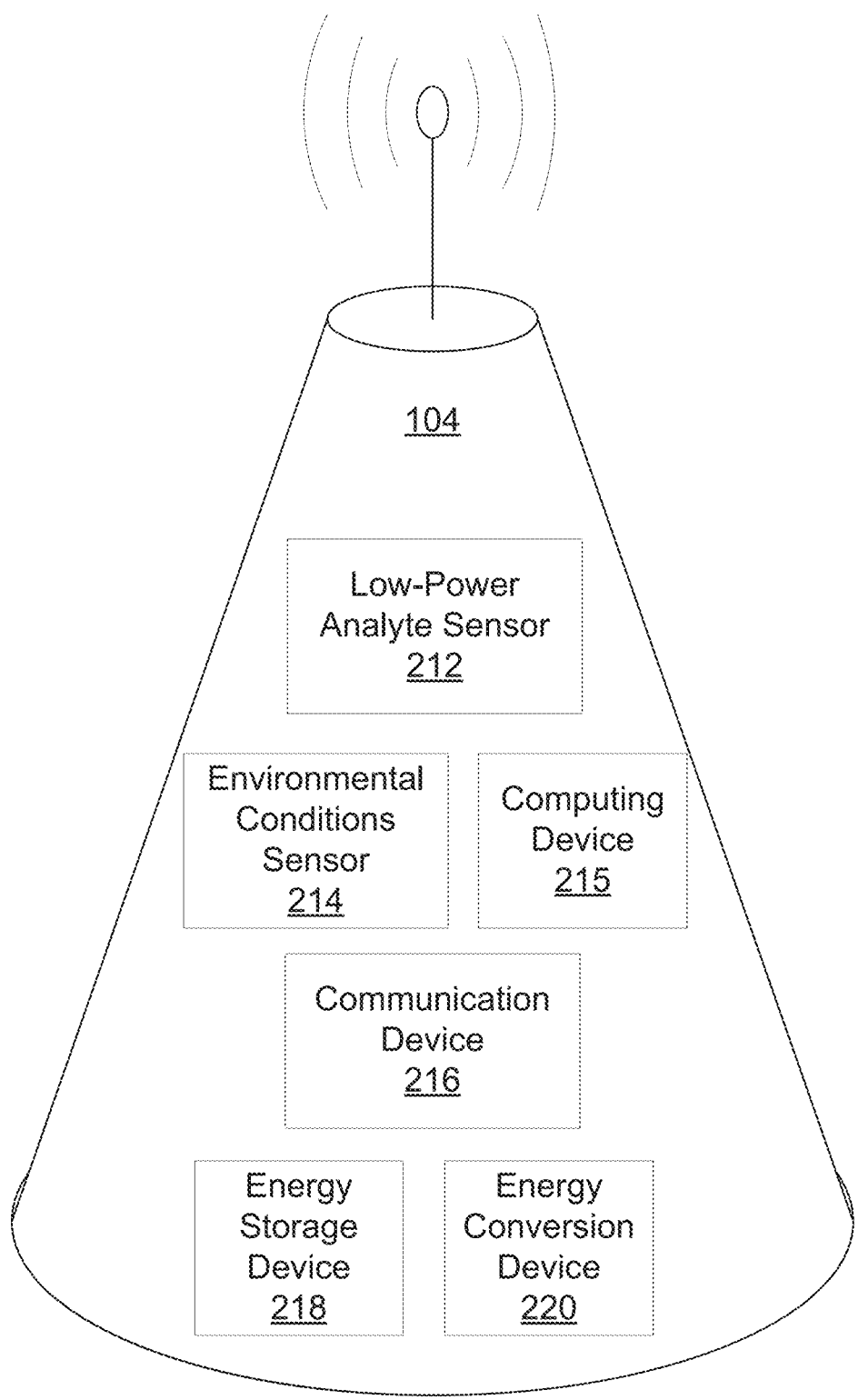
FIG. 2B illustrates a second node, in accordance with an embodiment of the present invention.
Figure 2C:
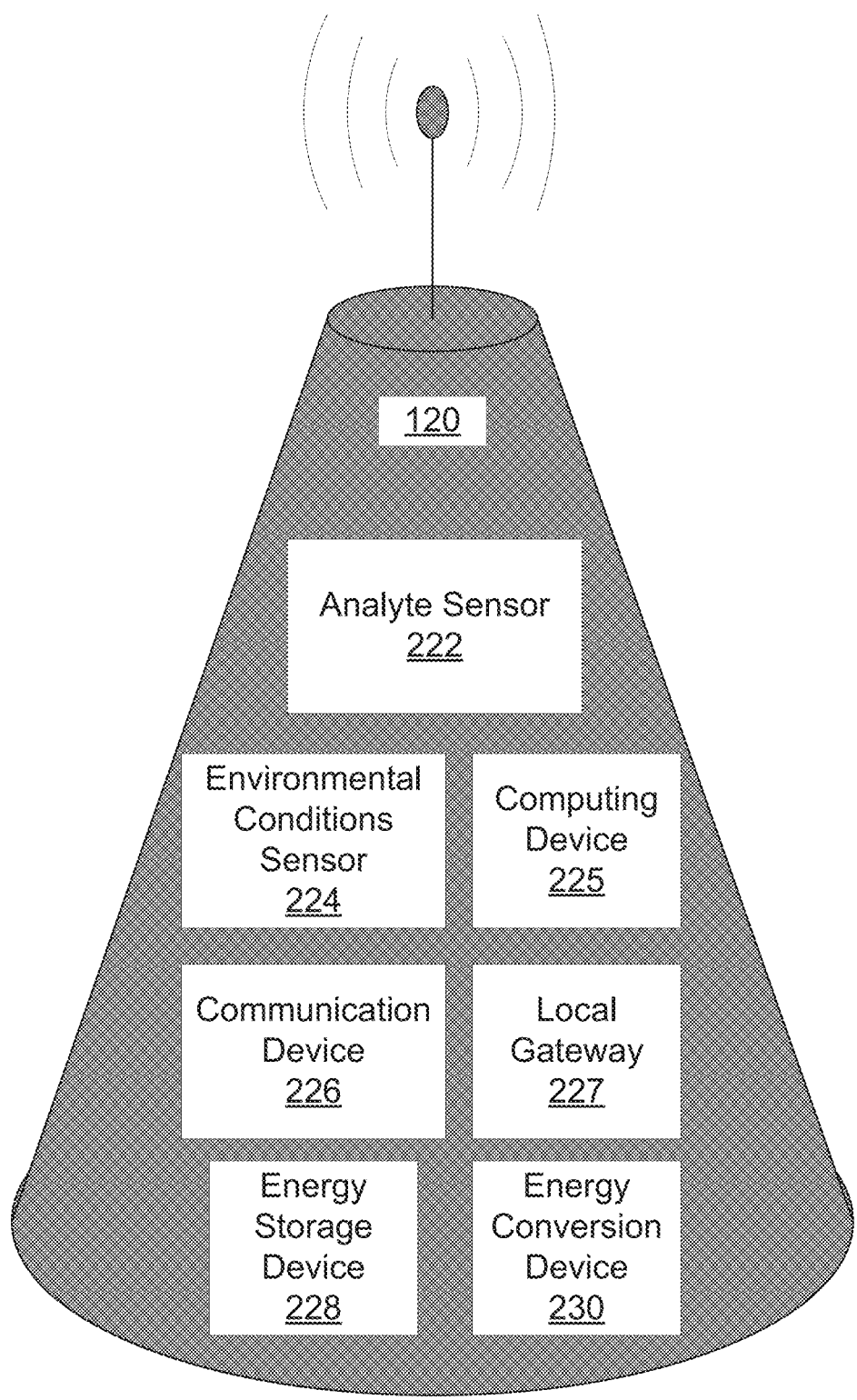
FIG. 2C illustrates a local gateway node, in accordance with an embodiment of the present invention.

Referring now to FIGS. 2A-2C, the first node 102, the second node 104, and the local gateway node 120 are shown, in accordance with an embodiment of the present invention. The first node 102, the second node 104, and the local gateway node 120 may include, for example, an analyte sensor, weather sensor, communication device, local gateway, energy storage device, energy conversion device, or any combination thereof.

FIG. 2A illustrates the first node 102, in accordance with an embodiment of the present invention. In an embodiment, the first node 102 may include a sensitive analyte sensor 202. In an embodiment, the first node 102 may include, for example, the sensitive analyte sensor 202, environmental conditions sensor 204, computing device 205, communication device 206, energy storage device 208, energy conversion device 210, or any combination thereof. For example, the first node 102 may include a sensitive analyte sensor 202 (e.g., an optical analyte sensor), a communication device 206 (e.g., an NFC device), and an energy storage device 208 (e.g., a battery).

In an embodiment, the first node 102 may include the sensitive analyte sensor 202. The sensitive analyte sensor 202 may detect an analyte or more than one analyte. In an embodiment, sensitive analyte sensor 202 may detect any analyte, such as, for example, thiols, alcohols, amines, carbonyl compounds, carboxylic acids, amino acids, carbohydrates, sulfur oxides, nitrogen oxides, fluorinated gases, aromatic compounds, aliphatic compounds, or any combination thereof. Nonlimiting examples of aliphatic compounds include methane, ethane, propane, and butane. For example, the sensitive analyte sensor 202 may detect only methane. In another example, the sensitive analyte sensor 202 may detect methane and nitrous oxide. In an embodiment, the sensitive analyte sensor 202 may be, for example, an optical analyte sensor. The sensitive analyte sensor 202 may have a minimum detection limit that may vary depending on the particular analyte being measured. For example, the sensitive analyte sensor 202 may have a lower detection limit for methane ranging from approximately 1 part per billion (ppb) to approximately 10 parts per million (ppm).

In an embodiment, the first node 102 may include the environmental conditions sensor 204. The environmental conditions sensor 204 may include, for example, a thermometer, a barometer, a hygrometer, an anemometer, or any combination thereof. The environmental conditions sensor 204 may determine one or more environmental conditions, such as, for example, temperature, humidity, wind speed, precipitation, dew point, pressure, solar irradiance, air quality, or snow depth. In another embodiment, the first node 102 may not include the environmental conditions sensor 204 and the one or more environmental conditions may be received via another device. For example, the first node 102 may receive the one or more environmental conditions from another node (e.g., the local gateway node 120, the second node 104, etc.) via the communication device 206. In an embodiment, the one or more environmental conditions determined by the environmental conditions sensor 204 and/or received from another node may be analyzed by the computing device 205.

Figure 6:
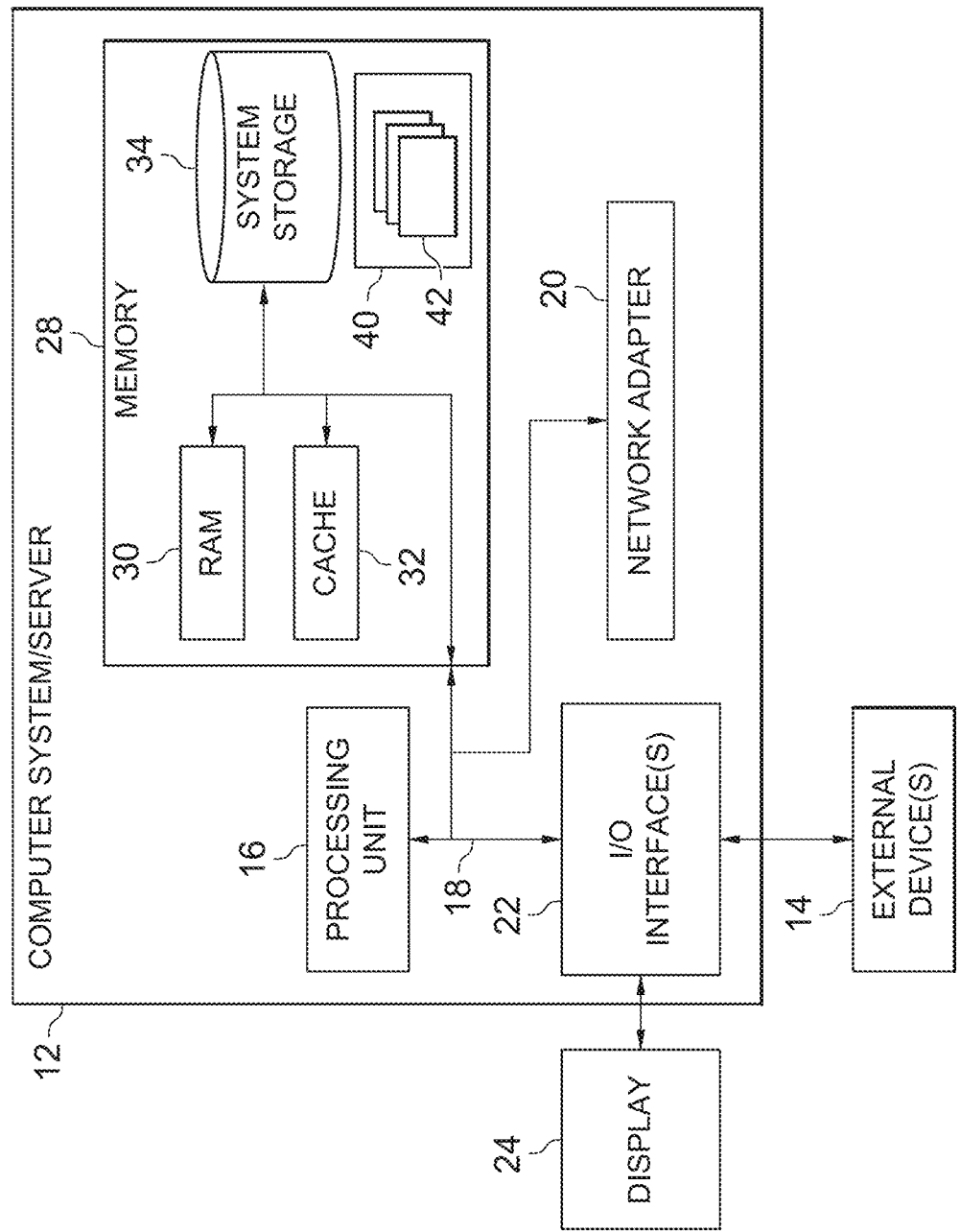
FIG. 6 depicts a block diagram of components of a proxy server computer executing the analyte monitoring program, in accordance with an embodiment of the present invention.

In an embodiment, the first node 102 may include the computing device 205. The computing device 205 may be, for example, computing node 10 (FIG. 6). The computing device 205 may include, for example, an analyte monitoring database, an environmental conditions database, a detection region database (e.g., including data associated with the region and a location of one or more nodes), one or more processors, and input/output interface (e.g., for transmitting and/or receiving data from one or more devices), or any combination thereof. The computing device 205 may transmit and/or receive data from one or more devices within the first node 102, such as, for example, the sensitive analyte sensor 202, the environmental conditions sensor 204, the communication device 206, or any combination thereof. The computing device 205 may store data received from the one or more devices in one or more databases, such as, for example, the analyte monitoring database, the environmental conditions database, the detection region database, or any combination thereof. The computing device 205 may analyze data received and/or stored in the one or more databases. For example, the computing device 205 may determine an analyte concentration based on data associated with an analyte (e.g., voltage data from the sensitive analyte sensor 202), data associated with one or more environmental conditions (e.g., wind speed data from the environmental conditions sensor 204 and/or solar irradiance data from the energy conversion device 210), or a combination thereof.

In an embodiment, the first node 102 may include the communication device 206. The communication device 206 may include, for example, a near-field communication (NFC) device, an IEEE 802.11 device (e.g., Wi-Fi), an IEEE 802.16 device (e.g., WiMAX), a Long Term Evolution (LTE) device, a microwave transmission device, or any combination thereof. The communication device 206 may enable communication with one or more nodes in the network (e.g., the local gateway node 120).

In an embodiment, the first node 102 may include the energy storage device 208, the energy conversion device 210, a hybrid energy storage/conversion device, or any combination thereof. The energy storage device 208 may be any device capable of storing energy (e.g., chemical energy, thermal energy, potential energy, etc.) for a period of time (e.g., hours, days, years, etc.). The energy conversion device 208 may be any device capable of converting an energy source to electrical energy. In an embodiment, the energy storage device 208 and the energy conversion device 210 may be separate devices. In an example, the energy storage device 208 may be a fuel tank (e.g., a gasoline tank) and the energy conversion device 210 may be a reciprocating engine. In another embodiment, the energy storage device 208 and the energy conversion device 210 may be the same device or an indistinguishable combination of devices (i.e. the hybrid energy storage/conversion device). Nonlimiting examples of the energy storage device 208, the energy conversion device 210, and the hybrid energy storage/conversion device include an electrochemical device, a photovoltaic device, a thermoelectric device, a piezoelectric device, a betavoltaic device, a turbine, a reciprocating engine, or any combination thereof. In an example, the hybrid energy storage/conversion device may be an electrochemical device (e.g., a battery) and the energy conversion device 210 may be a photovoltaic device (e.g., a solar cell).

FIG. 2B illustrates the second node 104, in accordance with an embodiment of the present invention. In a preferred embodiment, the second node 104 may include a low-power analyte sensor 212. In an embodiment, the second node 104 may include, for example, the low-power analyte sensor 212, environmental conditions sensor 214, computing device 215, communication device 216, energy storage device 218, energy conversion device 220, or any combination thereof. For example, second node 104 may include the low-power analyte sensor 212 (e.g., a chemiresistive analyte sensor), a communication device 216 (e.g., an NFC device), and an energy storage device 218 (e.g., a battery).

In an embodiment, the second node 104 may include the low-power analyte sensor 212. The low-power analyte sensor 212 may detect an analyte or more than one analyte. In an embodiment, low-power analyte sensor 212 may detect any analyte, such as, for example, thiols, alcohols, amines, carbonyl compounds, carboxylic acids, amino acids, carbohydrates, sulfur oxides, nitrogen oxides, fluorinated gases, aromatic compounds, aliphatic compounds, or any combination thereof. Nonlimiting examples of aliphatic compounds include methane, ethane, propane, and butane. For example, the low-power analyte sensor 212 may detect only methane. In another example, the low-power analyte sensor 212 may detect methane and nitrous oxide. In an embodiment, the low-power analyte sensor 212 may be, for example, a chemiresistive analyte sensor. The low-power analyte sensor 212 may have a minimum detection limit that may vary depending on the particular analyte being measured. For example, the low-power analyte sensor 212 may have a lower detection limit for methane ranging from approximately 1 part per million (ppm) to approximately 10 ppm.

In an embodiment, the second node 104 may include the environmental conditions sensor 214. The environmental conditions sensor 214 may include, for example, a thermometer, a barometer, a hygrometer, an anemometer, or any combination thereof. The environmental conditions sensor 214 may determine one or more environmental conditions, such as, for example, temperature, humidity, wind speed, precipitation, dew point, pressure, solar irradiance, air quality, or snow depth. In another embodiment, the second node 104 may include the environmental conditions sensor 214 and the one or more environmental conditions may be received via another device. For example, the second node 104 may receive the one or more environmental conditions from another node (e.g., the local gateway node 120, the first node 102, etc.) via the communication device 216. In an embodiment, the one or more environmental conditions determined by the environmental conditions sensor 214 or received from another node may be analyzed by the computing device 215.

In an embodiment, the second node 104 may include the computing device 215. The computing device 215 may be, for example, computing node 10 (FIG. 6). The computing device 215 may include, for example, an analyte monitoring database, an environmental conditions database, a detection region database (e.g., including data associated with the region and a location of one or more nodes), one or more processors, and input/output interface (e.g., for transmitting and/or receiving data from one or more devices), or any combination thereof. The computing device 215 may transmit and/or receive data from one or more devices within the second node 104, such as, for example, the low-power analyte sensor 212, the environmental conditions sensor 214, the communication device 216, or any combination thereof. The computing device 215 may store data received from the one or more devices in one or more databases, such as, for example, the analyte monitoring database, the environmental conditions database, the detection region database, or any combination thereof. The computing device 215 may analyze data received and/or stored in the one or more databases. For example, the computing device 215 may determine an analyte concentration based on data associated with an analyte (e.g., voltage data from the sensitive analyte sensor 202), data associated with one or more environmental conditions (e.g., wind speed data from the environmental conditions sensor 204 and/or solar irradiance data from, for example, a solar cell), or a combination thereof.

In an embodiment, the second node 104 may include the communication device 216. The communication device 216 may include, for example, a near-field communication (NFC) device, an IEEE 802.11 device (e.g., Wi-Fi), an IEEE 802.16 device (e.g., WiMAX), a Long Term Evolution (LTE) device, a microwave transmission device, or any combination thereof. The communication device 216 may enable communication with one or more nodes in the network (e.g., the local gateway node 120).

In an embodiment, the second node 104 may include the energy storage device 218, the energy conversion device 220, a hybrid energy storage/conversion device, or any combination thereof. The energy storage device 218 may be any device capable of storing energy (e.g., chemical energy, thermal energy, potential energy, etc.) for a period of time (e.g., hours, days, years, etc.). The energy conversion device 208 may be any device capable of converting an energy source to electrical energy. In an embodiment, the energy storage device 218 and the energy conversion device 220 may be distinct devices. For example, the energy storage device 208 may be a fuel tank (e.g., a gasoline tank) and the energy conversion device 210 may be a reciprocating engine. In another embodiment, the energy storage device 208 and the energy conversion device 210 may be the same device or an indistinguishable combination of devices (i.e. the hybrid energy storage/conversion device). Nonlimiting examples of the energy storage device 218, the energy conversion device 220, and the hybrid energy storage/conversion device include an electrochemical device, a photovoltaic device, a thermoelectric device, a piezoelectric device, a betavoltaic device, a turbine, a reciprocating engine, or any combination thereof. In an example, the hybrid energy storage/conversion device may be an electrochemical device (e.g., a battery) and the energy conversion device 220 may be a photovoltaic device (e.g., a solar cell).

FIG. 2C illustrates the local gateway node 120, in accordance with an embodiment of the present invention. In a preferred embodiment, the local gateway node 120 may include an analyte sensor 222. In an embodiment, the local gateway node 120 may include, for example, the analyte sensor 222, environmental conditions sensor 224, computing device 225, communication device 226, local gateway 227, energy storage device 228, energy conversion device 230, or any combination thereof. For example, local gateway node 120 may include the analyte sensor 222 (e.g., an optical analyte sensor, a chemiresistive analyte sensor, etc.), a communication device 226 (e.g., an NFC device), and an energy storage device 228 (e.g., a battery).

In an embodiment, the local gateway node 120 may include the analyte sensor 222. The analyte sensor 222 may be, for example, the sensitive analyte sensor 202, the low-power sensor 212, or a combination thereof.

In an embodiment, the local gateway node 120 may include the environmental conditions sensor 224. The environmental conditions sensor 224 may be, for example, the environmental conditions sensor 204, the environmental conditions sensor 214, or a combination thereof.

In an embodiment, the local gateway node 120 may include the computing device 225. The computing device 225 may be, for example, computing node 10 (FIG. 6). The computing device 225 may include, for example, an analyte monitoring database, an environmental conditions database, a detection region database (e.g., including data associated with the region and a location of one or more nodes), one or more processors, and input/output interface (e.g., for transmitting and/or receiving data from one or more devices), or any combination thereof. The computing device 225 may transmit and/or receive data from one or more devices within the local gateway node 120, such as, for example, the analyte sensor 222, the environmental conditions sensor 224, the communication device 226, the local gateway 227, or any combination thereof. The computing device 225 may store data received from the one or more devices in one or more databases, such as, for example, the analyte monitoring database, the environmental conditions database, the detection region database, or any combination thereof. The computing device 225 may analyze data received and/or stored in the one or more databases. For example, the computing device 225 may determine an analyte concentration based on data associated with an analyte (e.g., voltage data from the sensitive analyte sensor 202), data associated with one or more environmental conditions (e.g., wind speed data from the environmental conditions sensor 224 and/or solar irradiance data from the energy conversion device 230), or a combination thereof. In an embodiment, the computing device 225 may receive data from the local gateway 227 (e.g., received from a remote gateway) and perform one or more functions with the data, such as, for example, store the received data in one or more databases, analyze the received data, transmit the received data to another device, or any combination thereof.

In an embodiment, the local gateway node 120 may include the communication device 226. The communication device 226 may include, for example, a near-field communication (NFC) device, an IEEE 802.11 device (e.g., Wi-Fi), an IEEE 802.16 device (e.g., WiMAX), a Long Term Evolution (LTE) device, a microwave transmission device, or any combination thereof. The communication device 226 may enable communication with one or more nodes in the network (e.g., the first node 102, the second node 104, etc.).

In an embodiment, the local gateway node 120 may include the local gateway 227. The local gateway 227 may include one or more interfacing devices to enable communication with another network. The local gateway 227 may include one or more interfacing devices such as, for example, protocol translators, impedance matching devices, rate converters, fault isolators, signal translators, or any combination thereof. The local gateway 227 may communicate with one or more remote devices, such as, for example, a remote gateway, remote server, etc. The local gateway 227 may include one or more interfacing devices which may be compatible with one or more interfacing devices of the one or more remote devices. The local gateway 227 may transmit data obtained and/or determined by the analyte monitoring system 100. For example, one or more computing devices may determine than an analyte concentration in the detection region exceeds a threshold and the local gateway 227 may transmit data associated with the analyte concentration to a remote gateway of another network. Embodiments of the local gateway 227 transmitting analyte data to another network are described with respect to FIGS. 4A-4B.

In an embodiment, the local gateway node 120 may include the energy storage device 228, the energy conversion device 230, a hybrid energy storage/conversion device, or any combination thereof. The energy storage device 228 may be any device capable of storing energy (e.g., chemical energy, thermal energy, potential energy, etc.) for a period of time (e.g., hours, days, years, etc.). The energy conversion device 228 may be any device capable of converting an energy source to electrical energy. In an embodiment, the energy storage device 228 and the energy conversion device 230 may be distinct devices. In an example, the energy storage device 228 may be a fuel tank (e.g., a gasoline tank) and the energy conversion device 230 may be a reciprocating engine. In another embodiment, the energy storage device 228 and the energy conversion device 230 may be the same device or an indistinguishable combination of devices (i.e. the hybrid energy storage/conversion device). Nonlimiting examples of the energy storage device 228, the energy conversion device 230, and the hybrid energy storage/conversion device include an electrochemical device, a photovoltaic device, a thermoelectric device, a piezoelectric device, a betavoltaic device, a turbine, a reciprocating engine, or any combination thereof. In an example, the hybrid energy storage/conversion device may be an electrochemical device (e.g., a battery) and the energy conversion device 230 may be a photovoltaic device (e.g., a solar cell).

Figure 3A:
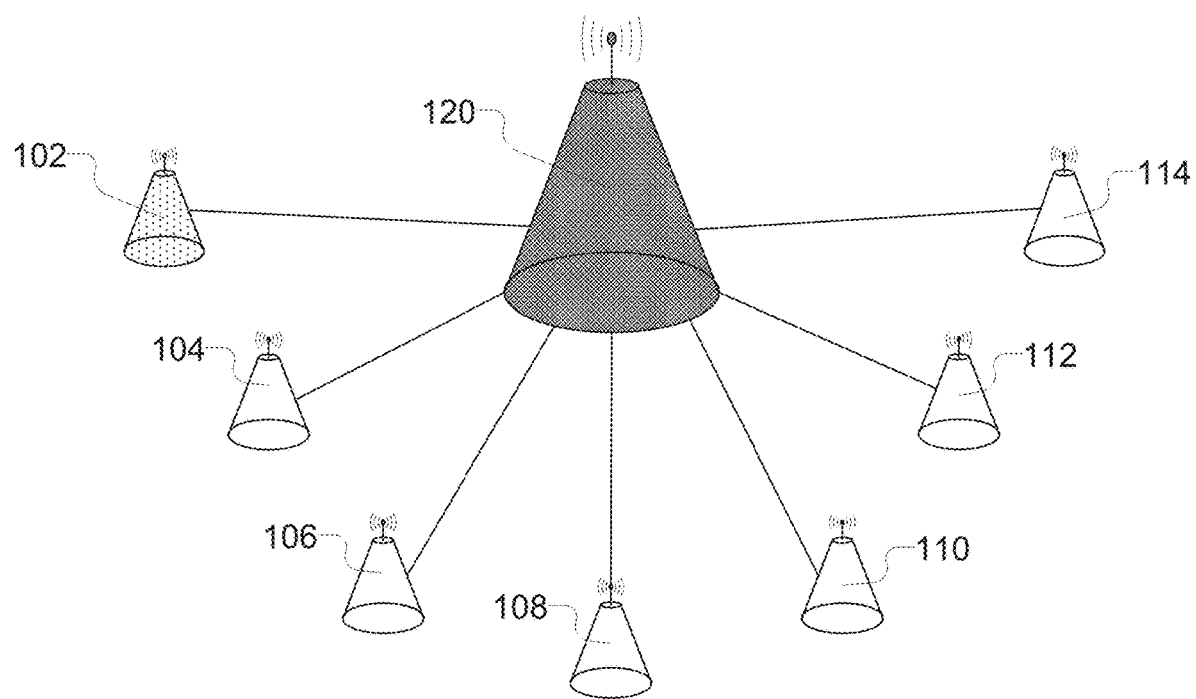
FIGS. 3A-3B illustrate the analyte monitoring system operating in a first mode, in accordance with an embodiment of the present invention.
Figure 3B:
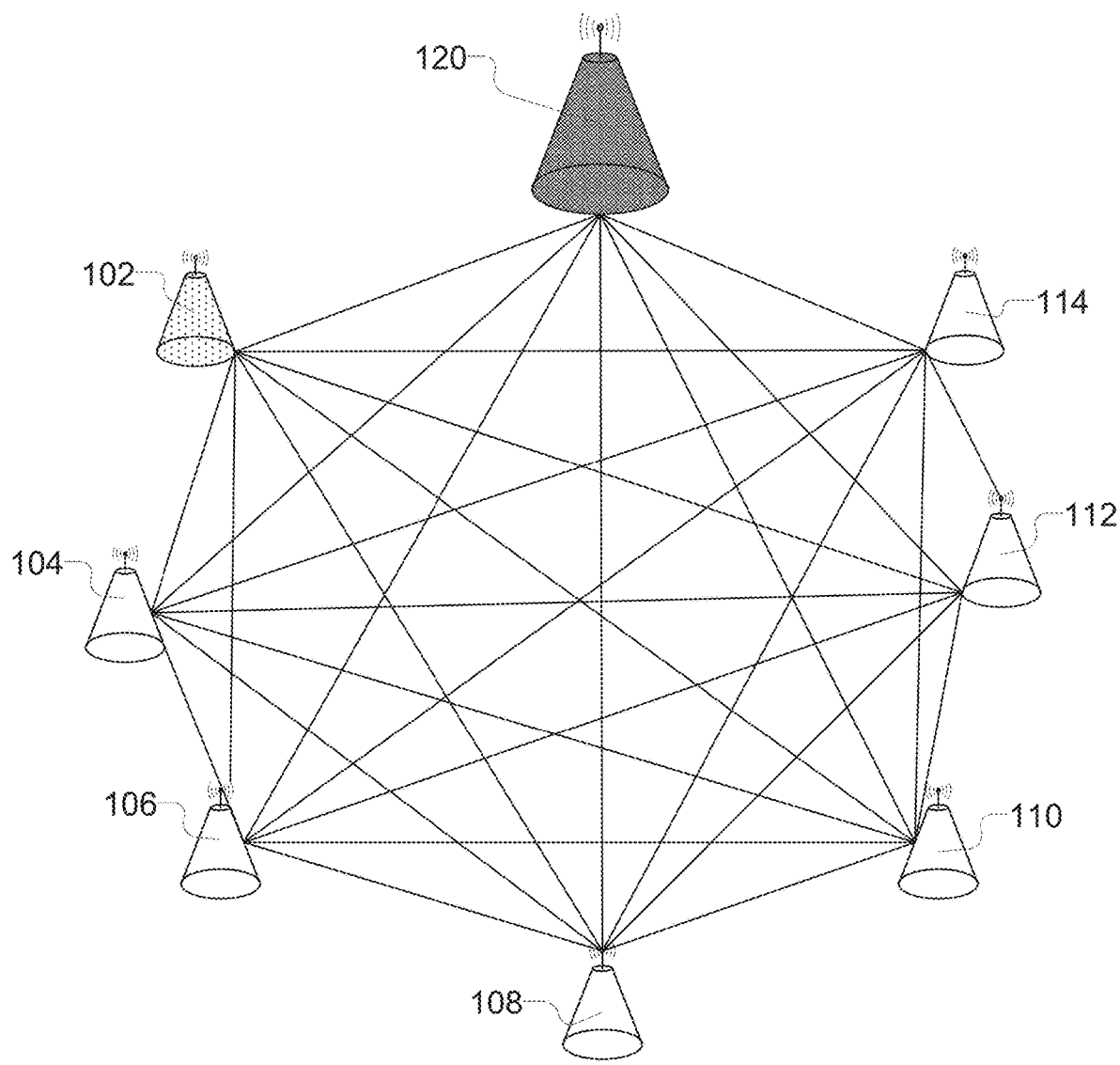

FIGS. 3A-3B illustrate the analyte monitoring system 100 (FIG. 1) operating in a first mode, in accordance with an embodiment of the present invention. The first mode may be performed by the analyte monitoring system 100 and include (1) detecting an analyte in the detection region, (2) generating an electrical signal in response to detecting the analyte, and (3) determining whether the electrical signal exceeds a threshold. In an embodiment, if the electrical signal is determined to exceed a threshold, the analyte monitoring system 100 may operate in a second mode or another mode. The second mode is described with reference to FIGS. 4A-4B. In an embodiment, the first mode may involve less power consumption than the second mode. In an embodiment, the first mode may involve less data transmission than the second mode. In an embodiment, the first mode may involve less power consumption and less data transmission than the second mode.

The analyte monitoring system 100 may be implemented using any network topology, such as, for example, bus, star, ring, mesh, tree, hybrid, daisy chain, or any combination thereof. A star network 300 (FIG. 3A) and a mesh network 350 (FIG. 3B) are described below.

FIG. 3A illustrates the analyte monitoring system 100 implemented in a star network 300. In the star network 300, one or more nodes (e.g., the first node 102, the second node 104, etc.) may be connected to another node (e.g., the local gateway node 120) with a point-to-point connection. In a preferred embodiment, the at least one first node (e.g., the first node 102) and the plurality of second nodes (e.g., the second node 104, the second node 106, etc.) may be connected to the local gateway (e.g., the local gateway 227 via the communication device 226 in the local gateway node 120). In an embodiment, every node may be directly connected to the local gateway node and indirectly connected to every other node via the local gateway node. In an embodiment, the star network 300 may be an extended star network including one or more repeaters between the local gateway node and one or more other nodes to extend a maximum transmission distance of the point-to-point links.

FIG. 3B illustrates the analyte monitoring system 100 implemented in a mesh network 350. In the mesh network 350, a plurality of nodes (e.g., e.g., the first node 102, the second node 104, etc.) may be interconnected to one another. In an embodiment, the mesh network 350 may be a fully connected network in which each node is connected with every other node with a point-to-point connection. In another embodiment, the mesh network 350 may be a partially connected network in which some nodes are connected to more than one other node in the network with a point-to-point connection.

Figure 4A:
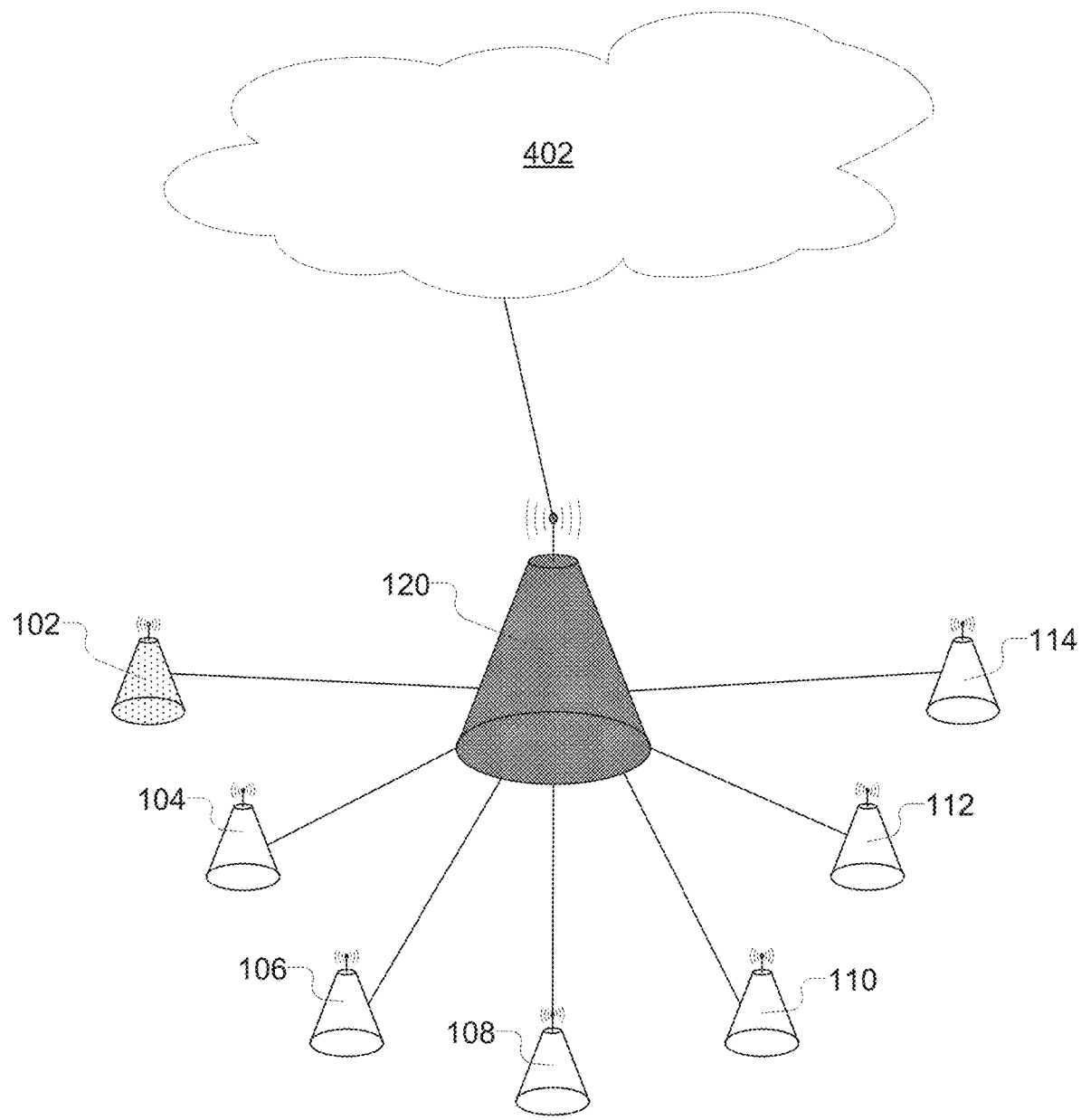
FIGS. 4A-4B illustrate the analyte monitoring system operating in a second mode, in accordance with an embodiment of the present invention.
Figure 4B:
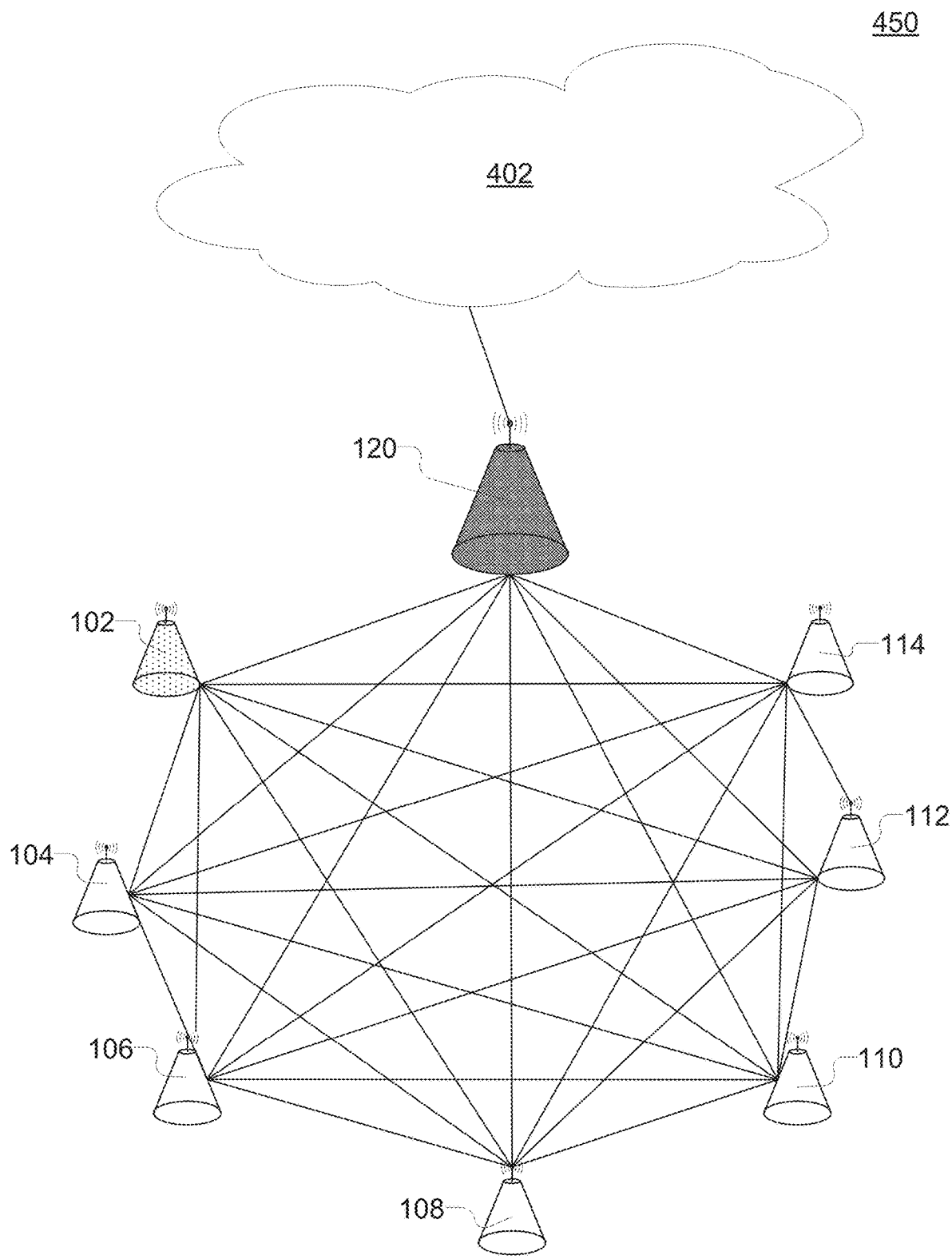

FIGS. 4A-4B illustrate the analyte monitoring system 100 operating in a second mode, in accordance with an embodiment of the present invention. In an embodiment, if a threshold is exceeded, the analyte monitoring system 100 may operate in the second mode or another mode. For example, if a determined electrical signal of an analyte sensor (e.g., sensitive analyte sensor 202, low-power analyte sensor 212, or analyte sensor 222) exceeds a threshold, the analyte monitoring system 100 may operate in the second mode. In another example, if a determined analyte concentration exceeds a threshold, the analyte monitoring system 100 may operate in the second mode. The second mode may include one or more of the following: (1) receiving data associated with one or more environmental conditions of the detection region and determining an analyte concentration based on one or more environmental conditions or (2) transmitting, by the local gateway, data associated with the analyte concentration. The second mode may consume more power than the first mode. By operating in the first mode unless a threshold is reached, the analyte monitoring system 100 may conserve power while accurately and swiftly detecting an analyte concentration exceeding a threshold.

In an embodiment, the second mode may involve receiving data associated with one or more environmental conditions. For example, an environmental conditions sensor (e.g., environmental conditions sensor 204, environmental conditions sensor 214, and/or environmental conditions sensor 224) may determine one or more environmental conditions and transmit data associated with the one or more environmental conditions to one or more computing devices (e.g., the computing device 205, computing device 215, and/or computing device 225). The one or more computing devices may determine an analyte concentration based on data received from an analyte sensor (e.g., voltage data) and the data associated with one or more environmental conditions. Utilizing an environmental conditions sensor and analyzing data associated with one or more environmental conditions may consume electrical power from, for example, a battery or another energy storage device. In another example, a local gateway (e.g., the local gateway 227) may request and receive data associated with one or more environmental conditions from a remote server. The local gateway may transmit the data associated with one or more environmental conditions to one or more computing devices. The one or more computing devices may determine an analyte concentration based on data received from an analyte sensor (e.g., voltage data) and the data associated with one or more environmental conditions. Utilizing the local gateway to retrieve data associated with one or more environmental conditions and analyzing the data may consume electrical power from, for example, a battery or another energy storage device.

In another embodiment, the second mode may involve data transmission. One or more nodes (e.g., the local gateway node 120) may transmit and/or receive data from a remote device (e.g., a remote server). In an embodiment, received data may be used to assist in determining a concentration of an analyte and/or a source of an analyte leak. For example, the local gateway 227 of the local gateway node 120 may communicate with a remote server. The local gateway 227 may transmit data associated with a detected analyte such as, for example, a voltage generated by an analyte sensor, a determined analyte concentration, or a combination thereof. The local gateway 227 may transmit a data query, such as, for example, a request for data associated with one or more environmental conditions of the detection region. The local gateway 227 may receive data from the remote server which may include data associated with for example, one or more environmental conditions of the detection region (e.g., wind distribution information). In an embodiment, data received from the server may validate a local node measurement. The local gateway 227 may receive a query from the remote server, such as, for example, data from a particular analyte sensor (e.g., determined analyte concentration at the first node 102). The local gateway 227 may receive an instruction from the remote server, such as, for example, detect an analyte at one or more nodes, determine an analyte concentration at one or more nodes, determine a distance between one or more nodes, or a combination thereof. Transmitting and receiving data between the local gateway 227 and the remote server and/or amongst various nodes may consume electrical power. An instruction to perform one or more tasks (e.g. detect an analyte at one or more nodes) may consume electrical power. Communicating with a remote server and/or performing additional tasks in the second mode may be more power intensive than operating in the first mode.

In an embodiment, one or more sensor nodes may determine a location of an analyte source. For example, data from one or more sensor nodes may be used to triangulate a location of the analyte source. One or more sensor nodes at particular locations may perform an analyte measurement in various arrangements to establish the localization of the source. One or more environmental conditions may be included in an analyte source determination, such as, for example, wind speed and wind direction. By determining an analyte concentration at one or more sensor nodes and accounting for wind speed and direction, a location of the analyte source may be determined. The location of the analyte source may be verified by repeating the localization determination by the same sensor nodes and/or different sensor nodes. In an embodiment, data associated with characteristics of the detection region may be taken into account in determining the location of the analyte source. Characteristics of the detection region may include, for example, topology, vegetation, infrastructure, or any combination thereof. Topology, vegetation, and infrastructure (e.g., a wall, building, etc.) that may change air flow in the detection region and affect a measurement depending on a location of the analyte leak. Characteristics of the detection region may be used to determine air flow changes caused by, for example, a building, and generate a plume distribution model based on the characteristics of the detection region. By determining an analyte concentration at one or more sensor nodes and accounting for characteristics of the detection region, a location of the analyte source may be determined. The data from sensor nodes may be transmitted to the central gateway to aggregate the data.

FIG. 5 is a flowchart of a method 500 for a multimodal analyte sensor network, using the analyte monitoring system 100 of FIG. 1, in accordance with an embodiment of the present invention. Steps of method 500 may be executed using a processor of a computer that encompasses, or is part of, the analyte monitoring system 100, or another system. In an embodiment, a method 500 for a multimodal analyte sensor network may include establishing an analyte sensor network in a detection region (step 504), a first mode 502, and a second mode 518. The first mode 502 may be less power intensive than the second mode 518.

Step 504 may include establishing an analyte sensor network in a detection region. Establishing the analyte sensor network in the detection region may involve installing an analyte sensor array. Establishing the analyte sensor network may include connecting one or more nodes of the analyte sensor array via a network. The analyte sensor array may include at least one first node and a plurality of second nodes. In an embodiment, one or more nodes may be connected and one or more nodes may not be connected to the network at a given time. The nodes that are connected to the network and acquiring signal may be dependent on the measurement of the node and the calculations that may indicate analyte level expected at the second nodes. If the measurement at a node is not significant, that nodes can enter in a remote low power mode state. The at least one first node may include a sensitive analyte sensor (e.g., an optical analyte sensor) having a lower detection limit than a low-power analyte sensor (e.g., a chemireisitive analyte sensor) included in the plurality of second nodes. Each node can carry out a calculation on the node based on the measurement and a plume distribution model. Each node may communicate via a communications device (e.g., an NFC device) with at least one other node (e.g, the local gateway node) in the network. At least one node may include a local gateway (e.g., the local gateway node) to communicate with a device (e.g., a remote server) outside of the network. Each node may be a distance (e.g., the distance $D_1$) from another node and distributed throughout the detection region.

The first mode 502 may include detecting an analyte in the detection region (step 508), generating an electrical signal in response to detecting the analyte (step 512), and determining whether the electrical signal exceeds a threshold (decision 516). In an embodiment, the analyte detection system 100 may remain in the first mode 502 if the threshold is not exceeded (decision 516, "No"). In another embodiment, the analyte detection system 100 may adjust to operating in a second mode 518 if the threshold is exceeded (decision 516, "Yes"). Each step and decision of the first mode 502 is discussed below.

Step 508 may include detecting an analyte in the detection region. Detecting may be performed by, for example, one or more analyte sensors (e.g., sensitive analyte sensor 202, low-power analyte sensor 212, etc.) in one or more nodes (e.g., first node 102, second node 104, etc.). Detecting may involve receiving an analyte into the sensor. The sensor may respond to receiving the analyte by generating an electrical signal as described in step 512 below.

Step 512 may include generating an electrical signal in response to detecting the analyte. Generating an electrical signal in response to receiving the analyte may involve an electrochemical response to receiving the analyte. For example, the sensor may include a chemiresistor which may change its electrical resistance in response to a chemical interaction between a sensing material (e.g., metal oxide, conductive polymer, carbon etc.) and the analyte. A resistance change may indicate a presence of analyte and/or an amount of analyte present. A change in electrical resistance (i.e. electrical signal) may be measured. The measured change of an electrical signal may be used, for example, to determine whether the electrical signal exceeds a threshold as described below with reference to decision 516.

Decision 516 may include determining whether the electrical signal exceeds a first threshold. If the electrical signal exceeds the first threshold, the analyte detection system 100 may adjust to operating in the second mode 518 (decision 516, Yes). If the electrical signal does not exceed the first threshold, the analyte detection system 100 may continue to operate in the first mode 502 (decision 502, No). The first threshold may be an electrical signal greater than, for example, a background signal. For example, a sensing material of a sensor may have an inherent resistance which may change in the presence of an analyte. A change in resistance measured (i.e. an electrical signal) that is greater than a typical variation of the inherent resistance may indicate that the analyte is present. In another example, one or more environmental conditions (e.g., temperature) may cause a change in a measured resistance greater than a typical variation. An electrical signal exceeding a threshold caused by one or more environmental conditions may be determined in the second mode 518 (e.g., decision 528, No) and result in reverting to operation in the first mode 502.

The second mode 518 may include receiving data associated with one or more environmental conditions of the detection region (step 520), determining an analyte concentration based on one or more environmental conditions (step 524), determining whether the analyte concentration exceeds a threshold (decision 528), and transmitting, by the local gateway, data associated with the analyte concentration (step 532). In an embodiment, the analyte detection system 100 may revert to the first mode if the analyte concentration is determined to not exceed a second threshold (decision 528, No). In an embodiment, the analyte detection system 100 remains in the second mode 518 if the analyte concentration is determined to exceed the second threshold (decision 528, Yes). Each step and decision of the second mode 518 is discussed below.

Step 520 may include receiving data associated with one or more environmental conditions of the detection region. In an embodiment, the data associated with the one or more environmental conditions may be received from an environmental conditions sensor (e.g., the environmental conditions sensor 204). Data associated with one or more environmental conditions may include, for example, data associated with temperature, pressure, humidity, etc. In an embodiment, the data associated with the one or more environmental conditions may be received from a remote server.

Step 524 may include determining an analyte concentration based on one or more environmental conditions. In an embodiment, one or more environmental conditions may be used to determine an analyte concentration. For example, an analyte detector may be sensitive to moisture such that data associated with a humidity and/or precipitation of a detection region may be used to exclude electronic signals resulting from moisture. In another example, data associated with wind speed may be used to estimate wind turbulence and mixing of an analyte caused by wind turbulence. In another example, data associated with solar irradiance may be used to estimate wind turbulence (e.g., from atmospheric heating near a ground surface) and mixing of an analyte caused by wind turbulence. Accounting for the one or more environmental conditions may enable more accurate determinations of an analyte concentration and/or reduce a likelihood of a false positive detection of an analyte.

Decision 528 may include determining whether the analyte concentration exceeds a second threshold. In an embodiment, the second threshold may be the lowest detectable concentration of an analyte by an analyte sensor (e.g., the sensitive analyte sensor 202, the low-power analyte sensor 212, etc.). In another embodiment, the second threshold may be a value for the analyte concentration that exceeds one standard deviation of a blank value. For example, a blank value may involve an analyte concentration determination in the absence of the analyte and one standard deviation of the blank value may be determined by a statistical evaluation of the analyte concentration determination in the absence of the analyte. In another embodiment, the second threshold may be a value for the analyte concentration that exceeds three standard deviations of a blank value. For example, a blank value may involve an analyte concentration determination in the absence of the analyte and three standard deviations of the blank value may be determined by a statistical evaluation of the analyte concentration determination in the absence of the analyte. In an embodiment, an analyte may be ubiquitous in the detection region and a threshold greater than one standard deviation above a background level of the analyte may be selected. The second threshold may be a fixed value or may change. For example, a sensing device may be recalibrated to determine a new blank value and the second threshold may change accordingly. In another example, a background level of an analyte may change and the second threshold may change accordingly. In another example, the local gateway (e.g., the local gateway 227) may receive an instruction to change the second threshold to another value. If the determined concentration does not exceed the threshold value, the analyte detection system may revert to the first mode 502 (e.g., by performing step 508). Reverting to the first mode 502 may be less power intensive than remaining in the second mode 518. If the determined analyte concentration exceeds the threshold value, the analyte detection system may perform step 532 (decision 528, yes).

Step 532 may include transmitting, by the local gateway, data associated with the analyte concentration. In an embodiment, the data associated with the analyte concentration may include, for example, the determined analyte concentration, a change in the determined concentration over time, a measurement of the generated electrical signal, a change in the measurement of the generated electrical signal over time, a location of one or more node(s) where a detection occurred, one or more environmental conditions, the first threshold, the second threshold, an alert indicating an exceedance of a threshold, or any combination thereof. In an embodiment, the analyte detection system may transmit data associated with the analyte concentration to a remote server. In an embodiment, the analyte detection system 100 may receive a request for additional data (e.g., one or more data associated with the analyte concentration not previously sent) and/or an instruction to perform one or more functions (e.g., detect an analyte at a particular node). The analyte detection system 100 may transmit additional data in response to a request and/or perform one or more functions in response to an instruction to do so. In an embodiment, a concentration and location of an analyte leak may be determined by a central computer (e.g., at the local gateway node) based on information requested from the individual nodes. In another embodiment, a central computer may carry out a model calculation of the distribution of the plume from an analyte leak situated in the detection platform and compare the calculation with data received from the sensing nodes. If the values are similar, the system may validate the model. If the measurement and model values are different, data from each sensor except for one excluded sensor may be used to generate a second model. The second model may be used to determine an analyte concentration value for the location of the excluded sensor. The analyte concentration value for the location of the excluded sensor may be compared with the value measured by the excluded sensor. If the second model predicts the value measured by the excluded sensor within a margin of error, the second model may be authorized to predict one or more additional concentrations of an analyte, determine the location and/or movement of an analyte plume, determine a location of an analyte leak, or any combination thereof. The calculation may be iterated until the model output confirms a measurement of one or more analyte sensors. In the above determination, the model may be continuously updated with data associated with one or more environmental conditions and a concentration of analyte detected by one or more analyte sensors. If the model indicates that nodes in the sensor network are not in the direction of plume dispersion those sensing nodes may be excluded from the network to save energy. Step 532 may involve more data transfer and energy consumption than, for example, any step in the first mode 502. Transferring substantial data and/or consuming substantial energy in step 532 may be acceptable since a statistically significant likelihood (e.g., based on a first threshold and a second threshold) that an analyte is present in the detection region may exist. By avoiding substantial data transfer and/or substantial energy consumption until a statistically significant likelihood that an analyte is present in the detection region, the analyte detection system 100 may avoid unnecessary resource utilization.

Referring to FIGS. 1-5, embodiments of the present invention include an analyte sensor network operating in a first mode and a second mode. In an embodiment, the analyte sensor network may switch from operating in the first mode to operating in the second mode if a first threshold is exceeded (e.g., a voltage of an electrical signal outside one standard deviation of a blank value). In another embodiment, the analyte sensor network may switch from operating in the second mode to operating in the first mode if a second threshold is not exceeded (e.g., a determined analyte concentration does not exceed one standard deviation of a blank value). In an embodiment, operating in the first mode may require less resource utilization than operating in the second mode. For example, in comparison to operating in the second mode, operating in the first mode may involve, for example, less energy consumption, less data transmission (e.g., no data transmission between the nodes), less use of computing resources (e.g., a processor may only determine whether a voltage of an electrical signal exceeds a first threshold), and less frequent detection of an analyte by analyte sensors (e.g., an analyte sensor may only detect an analyte once per day). The analyte sensor network may operate in the first mode at a lower operating cost (e.g., lower energy and/or maintenance cost) than if the analyte sensor network is operating in the second mode. If a second threshold is exceeded, a significant probability exists that an analyte leak may exist. Thus, additional resources (e.g., energy, data transmission, computing resources, detection frequency, etc.) may be employed if a significant probability exists that an analyte leak exists (i.e., if the second threshold is exceeded). By allocating less resources to the first mode and more resources to the second mode, the analyte sensor network may operate more efficiently and at less cost.

Referring now to FIG. 6, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 6, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Based on the foregoing, a computer system, method, and computer program product have been disclosed. However, numerous modifications and substitutions can be made without deviating from the scope of the present invention. Therefore, the present invention has been disclosed by way of example and not limitation.

What is claimed is:

1. A system for detecting an analyte in a detection region, the system comprising:
    an analyte sensor array comprising at least one first node and a plurality of second nodes distributed throughout the detection region,
    wherein the at least one first node comprises an optical sensor, and wherein each node of the plurality of second nodes comprises a chemiresistive sensor;
    an environmental conditions measuring device comprising at least one of a thermometer, a barometer, a hygrometer, or an anemometer;
    a local gateway configured to communicate with a remote gateway;
    a computing device comprising one or more processors, computer-readable storage media, and program instructions stored on the computer-readable storage media for execution by the processor, the program instructions comprising instructions to:
        operate in a first mode comprising instructions to:
            detect the analyte with the analyte sensor array established within the detection region, wherein the instructions to detect the analyte comprise instructions to identify an electrical signal generated by an electrochemical reaction of the analyte with a first analyte sensor or a second analyte sensor;
in response to the electrical signal exceeding a first threshold value, operate in a second mode comprising instructions to:
request data associated with one or more environmental conditions of the detection region;
determine an analyte concentration based on the one or more environmental conditions; and
transmit, by the local gateway, data associated with the analyte concentration in response to the analyte concentration exceeding a second threshold value.

2. The system of claim 1, wherein at least one processor of the one or more processors are within at least one node of the at least one first node and the plurality of second_nodes.

3. The system of claim 1, wherein the instructions to determine the analyte concentration based the on one or more environmental conditions comprise instructions to:
receive, by the one or more computer processors, analyte monitoring data from at least one of the first analyte sensor or the second analyte sensor;
calculate, by the one or more computer processors, a value for the analyte concentration based, in part, on data associated with the one or more environmental conditions of the detection region; and
identify, by the one or more computer processors, if the value is greater than one standard deviation of a blank value.

4. A system comprising:
an analyte sensor array comprising at least one first node and a plurality of second nodes distributed throughout the detection region, wherein at least one node of the plurality of second nodes comprises a chemiresistive sensor;
an environmental conditions measuring device; and
a computing device comprising one or more processors, computer-readable storage media, and program instructions stored on the computer-readable storage media for execution by the processor, the program instructions comprising instructions to:
operate in a first mode comprising instructions to:
detect an analyte with the analyte sensor array;
wherein the program instructions comprise instructions to identify an electrical signal generated by an electrochemical reaction of the analyte with a first analyte sensor or a second analyte sensor;
in response to the electrical signal exceeding a first threshold value, operate in a second mode comprising instructions to:
determine an analyte concentration based of the analyte detected by the analyte sensor array and one environmental condition; and
transmit, by a local gateway, analyte concentration data.

5. The system of claim 4, wherein the at least one first node comprises an optical sensor.

6. The system of claim 4, wherein two or more of the plurality of second nodes comprises a chemiresistive sensor.

7. The system of claim 4, wherein the local gateway is in communication with a remote gateway, and wherein the instructions to transmit analyte concentration data comprise instructions to transmit the analyte concentration data to the remote gateway.

8. The system of claim 4, wherein at least one processor of the one or more processors are within at least one node of the at least one first node and the plurality of second nodes.

9. The system of claim 4, wherein the instructions to determine the analyte concentration comprise instructions to:
receive, by the one or more computer processors, analyte monitoring data from at least one of a first analyte sensor or a second analyte sensor;
calculate, by the one or more computer processors, a value for the analyte concentration based, in part, on data associated with the one or more environmental conditions of the detection region; and
identify, by the one or more computer processors, if the value is greater than one standard deviation of a blank value.

* * * * *